(12) United States Patent
Swaminathan

(10) Patent No.: US 9,801,565 B2
(45) Date of Patent: Oct. 31, 2017

(54) METHODS AND WORKFLOW DESIGN FOR IMPROVING SPECIFICITY OF BREAST MR

(75) Inventor: Srirama V. Swaminathan, Monmouth Junction, NJ (US)

(73) Assignee: Koninklijke Philips N.V., Eindhoven (NL)

( * ) Notice: Subject to any disclaimer, the term of this patent is extended or adjusted under 35 U.S.C. 154(b) by 2330 days.

(21) Appl. No.: 12/160,894

(22) PCT Filed: Jan. 8, 2007

(86) PCT No.: PCT/US2007/060209
§ 371 (c)(1),
(2), (4) Date: Jul. 15, 2008

(87) PCT Pub. No.: WO2007/089954
PCT Pub. Date: Aug. 9, 2007

(65) Prior Publication Data
US 2008/0306374 A1 Dec. 11, 2008

Related U.S. Application Data

(60) Provisional application No. 60/763,416, filed on Jan. 30, 2006.

(51) Int. Cl.
*A61B 5/055* (2006.01)
*G01R 33/3415* (2006.01)
*G01R 33/561* (2006.01)

(52) U.S. Cl.
CPC .......... *A61B 5/055* (2013.01); *G01R 33/3415* (2013.01); *G01R 33/5611* (2013.01); *A61B 5/0555* (2013.01)

(58) Field of Classification Search
USPC ................. 600/407, 409, 410, 422, 425
See application file for complete search history.

(56) References Cited

U.S. PATENT DOCUMENTS 5,416,413 A    5/1995  Leussler
6,943,033 B2 *  9/2005  Van Zijl et al. .............. 436/173
(Continued)

FOREIGN PATENT DOCUMENTS

EP    1312307 A2    5/2003

OTHER PUBLICATIONS

Friedman, P. D., et al.; Technical Innovation-SENSE Imaging of the Breast; 2005; AJR; 184:448-451.
(Continued)

*Primary Examiner* — Rochelle Turchen

(57) ABSTRACT

In a breast imaging method, magnetic resonance data are acquired of one or both breasts of a subject (16) using a breast coil (20, 20') coupled with said one or both breasts. The acquiring employs at least four independent channels (41, 42, 43, 44, 45, 46; 61, 62, 63, 64, 65, 66) per breast. The acquired magnetic resonance data are processed to generate at least one of (i) an image, (ii) a spectrum, and (iii) elasticity data. The at least four independent channels per breast are suitably embodied as a dual breast coil (20) including left breast conductors (31, 32, 33, 34, 35, 36) defining at least four independent left breast acquisition channels (41, 42, 43, 44, 45, 46) and right breast conductors (51, 52, 53, 54, 55, 56) defining at least four independent right breast acquisition channels (61, 62, 63, 64, 65, 66).

14 Claims, 3 Drawing Sheets

(56) References Cited

U.S. PATENT DOCUMENTS

Figure 1:
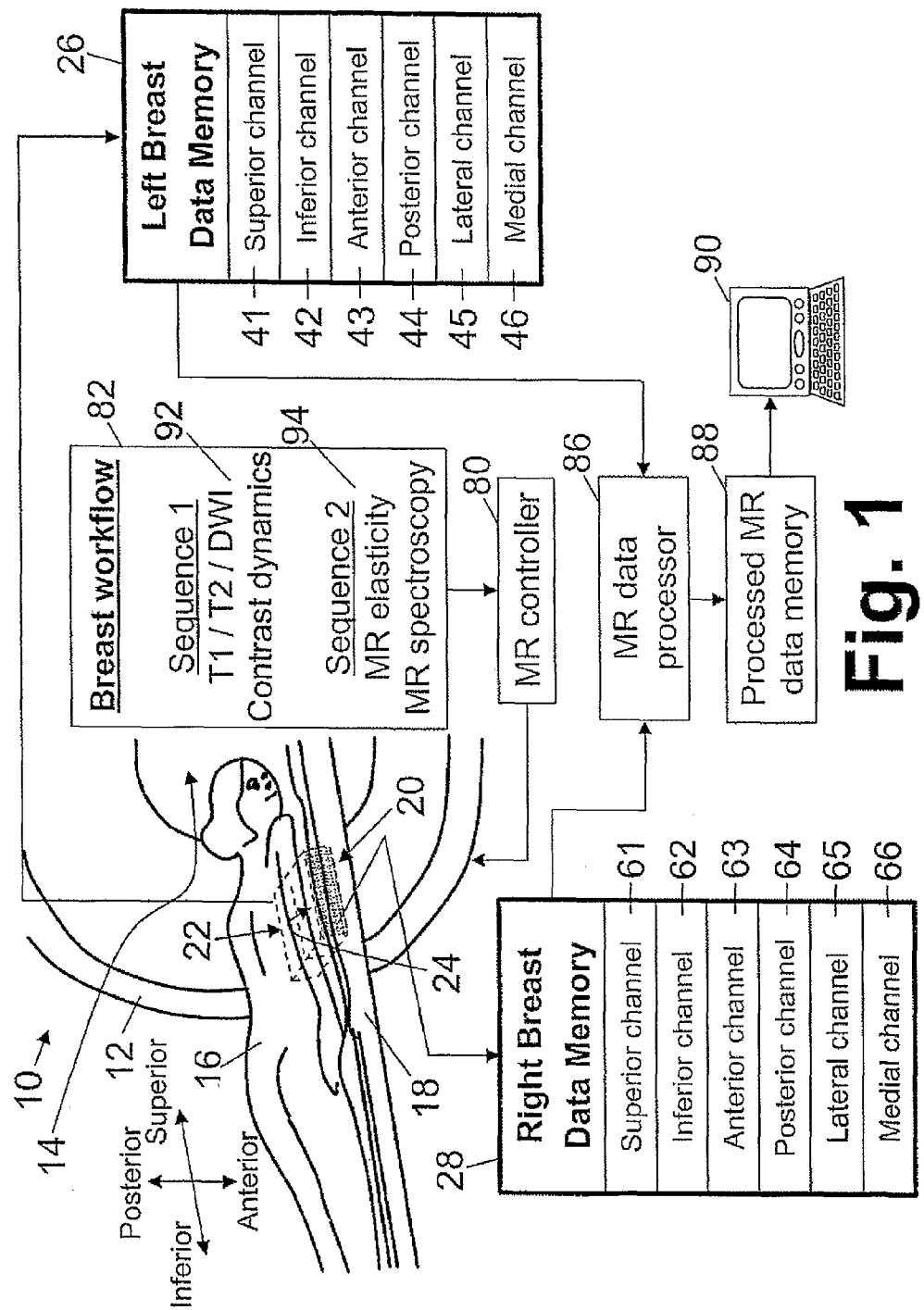

| | | | |
|---|---|---|---|
| 2001/0039378 A1 | 11/2001 | Lampman et al. | |
| 2002/0042569 A1* | 4/2002 | Wedeen | 600/411 |
| 2002/0103428 A1* | 8/2002 | deCharms | 600/410 |
| 2003/0135106 A1* | 7/2003 | Edelman | 600/410 |
| 2004/0073106 A1* | 4/2004 | Lee et al. | 600/415 |
| 2004/0254444 A1 | 12/2004 | Bittner | |
| 2005/0104591 A1* | 5/2005 | Qu et al. | 324/318 |
| 2005/0245805 A1 | 11/2005 | Hoppel et al. | |
| 2006/0012367 A1* | 1/2006 | Meaney et al. | 324/315 |
| 2006/0094952 A1* | 5/2006 | Ma et al. | 600/410 |

OTHER PUBLICATIONS

Knowles, A., et al.; Application of SENSE for High Spatial and Temporal MR Imaging of the Breast; 2003; ISMRM.

Orel, S. G., et al.; MR Imaging of the Breast for the Detection, Diagnosis, and Staging of Breast Cancer; 2001; Radiology; 220:13-30.

Pruessmann, K. P., et al.; SENSE: Sensitivity Encoding for Fast MRI; 1999; MRM: 42:952-962.

Sinkus, R., et al.; High-resolution tensor MR eleastography for breast tumour detection; 2000; Phys. Med. Biol.; 45:1649-1664.

CONFIRMA "SureLoc" Console—CADstream's Interventional Guidance Tool; http://www.confirma.com/products sureloc.html.

Invivo Philips 1.5T "Achieva" 7 channel biopsy breast array; http://www.invivocorp.com/products/CoilProductDetail.

Invivo Siemens 1.5T "Symphony" 7 channel biopsy breast array; http://www.invivocorp.com/products/CoilProductDetail.

Invivo GE 1.5T "Excite" 7 channel biopsy breast array http://www.invivocorp.com/products/CoilProductDetail.

* cited by examiner

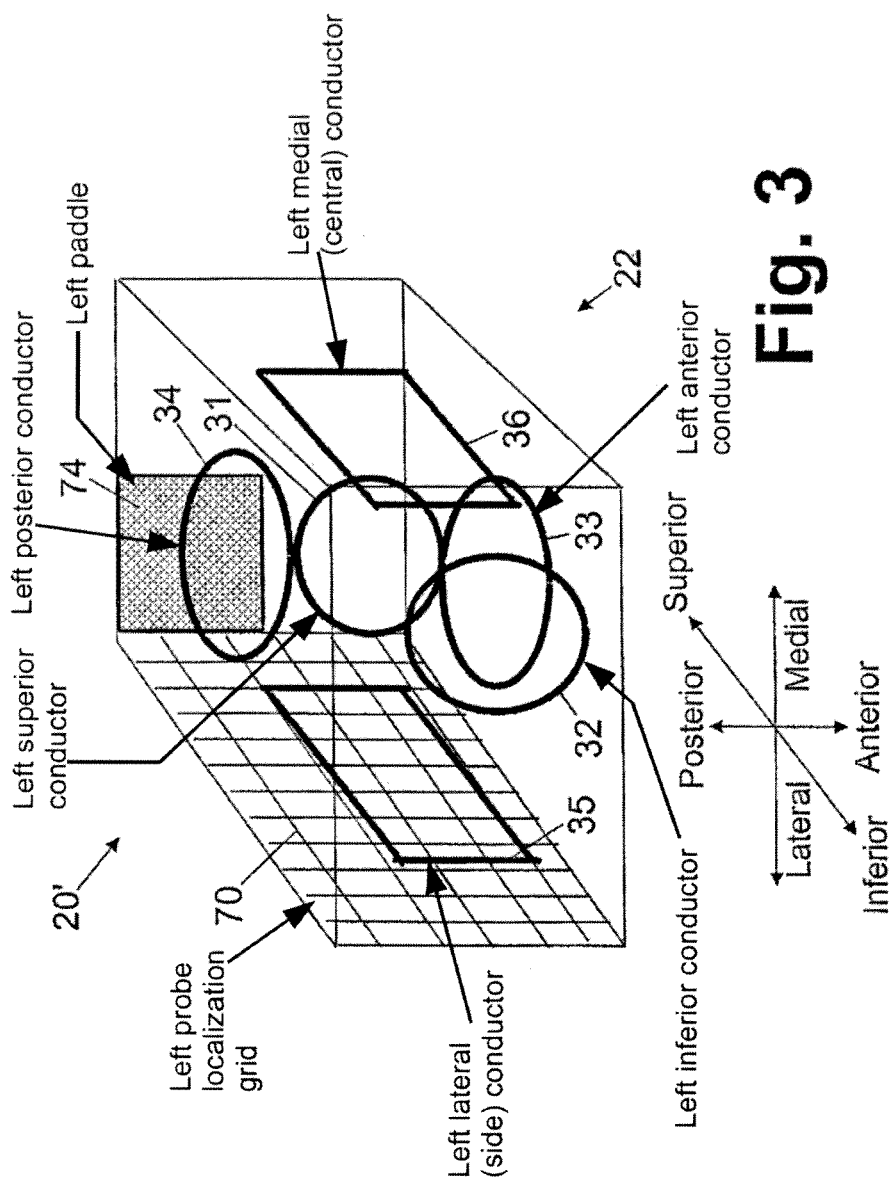

METHODS AND WORKFLOW DESIGN FOR IMPROVING SPECIFICITY OF BREAST MR

The following relates to the medical imaging and diagnosis arts. It finds application in magnetic resonance-based screening or diagnosis of breast cancers or other breast malignancies, in breast coils for performing same, in magnetic resonance scanner systems configured to perform same, and in magnetic resonance scanner systems employing breast coils.

At the present time, the dominant modalities for screening for breast cancer are mammography and ultrasound. These breast screening techniques suffer from low sensitivity in detecting tumors, and poor specificity in determining whether a detected tumor is benign or malignant.

Magnetic resonance imaging (MRI) has also been proposed as a modality for breast cancer screening and diagnosis. MRI has relatively high sensitivity as compared with mammography and ultrasound, but suffers from a poor specificity typically in a range of between 30% and 60%. This poor specificity coupled with the high cost and low throughput of MRI has limited MRI to a supporting role in breast cancer diagnosis. MRI is sometimes applied to women at high risk for breast cancer, but is typically not used for general breast cancer screening.

When MRI indicates a possible malignant breast tumor, a biopsy is typically performed to make a more definitive determination as to whether the detected tumor is benign or malignant. The poor specificity of MRI therefore leads to a correspondingly high number of biopsies of tumors which ultimately are determined to be benign. Thus, the poor specificity of MRI produces extraneous interventional biopsy procedures and undue stress on women who are initially wrongly diagnosed as having breast cancer based on the MRI results.

In view of the foregoing, the application of MRI to breast cancer screening would be facilitated by improved specificity in distinguishing malignant from benign tumors, and would further be facilitated by a more efficient workflow for MRI-based breast cancer screening.

The following contemplates improved apparatuses and methods that overcome the aforementioned limitations and others.

According to one aspect, a breast imaging method is disclosed. Magnetic resonance data are acquired of one or both breasts of a subject using a breast coil coupled with said one or both breasts. The acquiring employs at least four independent channels per breast. The acquired magnetic resonance data are processed to generate at least one of (i) an image, (ii) a spectrum or spectra, and (iii) elasticity data and images.

According to another aspect, a magnetic resonance system is disclosed for performing a breast imaging method as set forth in the preceding paragraph.

According to another aspect, a dual breast coil is disclosed for use in magnetic resonance breast imaging. The dual breast coil includes left-breast conductors configured to couple with the left breast. The left-breast conductors define at least four independent left-breast acquisition channels for acquiring magnetic resonance data from the left breast. The dual breast coil further includes right-breast conductors configured to couple with the right breast. The right-breast conductors define at least four independent right-breast acquisition channels for acquiring magnetic resonance data from the right breast.

According to another aspect, a magnetic resonance system is disclosed, including a magnetic resonance scanner, and a dual breast coil as set forth in the preceding paragraph.

One advantage resides in improved specificity in magnetic resonance-based breast cancer screening and diagnosis.

Another advantage resides in improved workflow for magnetic resonance-based breast cancer screening and diagnosis.

Another advantage resides in increased patient throughput in magnetic resonance-based breast cancer screening and diagnosis.

Another advantage resides in reduced cost of magnetic resonance-based breast cancer screening and diagnosis.

Another advantage resides in reduction of unwanted invasive procedures such as biopsies and needle localizations.

Numerous additional advantages and benefits will become apparent to those of ordinary skill in the art upon reading the following detailed description of the preferred embodiments.

The invention may take form in various components and arrangements of components, and in various process operations and arrangements of process operations. The drawings are only for the purpose of illustrating preferred embodiments and are not to be construed as limiting the invention.

FIG. 1 diagrammatically shows a magnetic resonance scanning system for performing breast cancer screening and diagnosis.

Figure 2:
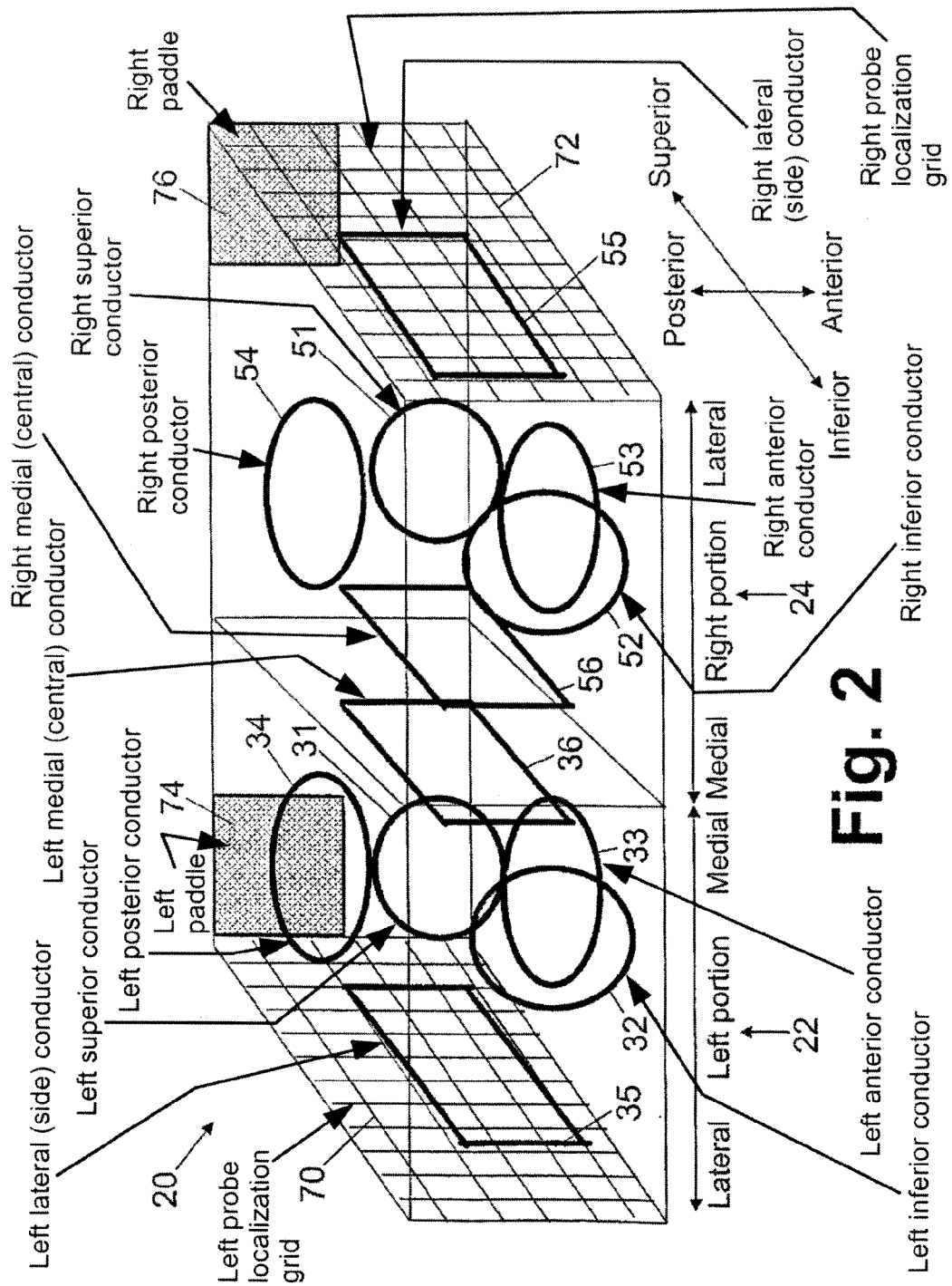

FIG. 2 diagrammatically shows the dual breast coil used in the magnetic resonance scanning system of FIG. 1.

FIG. 3 diagrammatically shows an alternative single breast coil suitable for imaging the left breast.

With reference to FIG. 1, a magnetic resonance scanner 10 is diagrammatically indicated by showing a portion of the scanner housing 12 defining a scanner bore 14 configured to receive a subject 16 that is to undergo breast cancer screening, breast cancer diagnosis, or other breast imaging or characterization. The subject 16 is disposed on a support 18, such as a table, couch, or so forth. The illustrated support 18 is configured to receive the subject 16 lying face-down so that the breasts of the subject 16 face the support 18. The support 18 includes a recess containing a dual breast coil 20 (indicated in phantom in FIG. 1) that receives the breasts of the face-down subject 16. The illustrated support 18 has a surface configured to conform with the exterior form of the subject 16 to promote secure and stationary positioning of the subject 16 on the support 18. The subject 16 is optionally partially immobilized or restrained by straps or other restraints (not shown) so that the breasts remain stationary within the dual breast coil 20. For convenience, the superior/inferior (i.e., head/foot) directions and the anterior/posterior (i.e., front-back) directions of the subject 16 are indicated in FIG. 1. The dual breast coil 20 includes a left-hand portion 22 configured to receive the left breast, and a right-hand portion 24 configured to receive the right breast.

The left-hand portion 22 couples with the left breast at the magnetic resonance frequency to acquire magnetic resonance data of the left breast that is stored in a left breast data memory 26, while the right-hand portion 24 couples with the right breast at the magnetic resonance frequency to acquire magnetic resonance data of the right breast that is stored in a right breast data memory 28. The left and right breast data memories 26, 28 may be logical partitions of a common memory (which may be, for example, a magnetic disk memory, an optical disk memory, a random access memory, an electrostatic memory, or so forth), or may be physically separate memories.

The subject 16 is shown in FIG. 1 outside of the scanner bore 14. Typically, the support 18 is linearly translatable to insert the subject 16 into the scanner bore 14. For example, the subject 16 is suitably translated along the superior direction of the subject 16 to insert the subject 16 into the scanner bore 14. The housing 12 of the magnetic resonance scanner 10 contains or supports various components used in generating, spatially encoding, and acquiring magnetic resonance signals from the inserted subject 16. Typically, the magnetic resonance scanner 10 includes a main superconducting or resistive magnet (not shown) housed in the housing 12 for generating a static main ($B_0$) magnetic field in an examination region within the scanner bore 14. One or more radio frequency coils 20 are used to generate and/or detect radio frequency ($B_1$) excitations in the subject 16 or in a selected portion thereof (such as a portion or all of the breasts of the subject 16). In some embodiments, the dual breast coil 20 is used both for exciting and reading magnetic resonance signals. In other embodiments, the dual breast coil 20 is used to read magnetic resonance signals that are excited by another radio frequency coil, such as a whole-body coil (not shown) disposed on or inside of the scanner housing 12. The magnetic resonance scanner 10 further includes magnetic field gradient coils (not shown), typically disposed in the scanner housing 12, for imposing magnetic field gradients on the main ($B_0$) magnetic field so as to spatially encode the generated and detected magnetic resonance signals.

FIG. 1 shows example magnetic resonance scanner 10 having a closed cylindrical bore. However, the workflows, imaging techniques, breast coils 20, and so forth disclosed herein can be employed in conjunction with substantially any type of magnetic resonance scanner, such as an open-bore cylindrical scanner, a vertical-bore scanner, or so forth. Moreover, while a horizontal face-down subject arrangement is shown in example FIG. 1, other subject arrangements are also contemplated. For example, when using the illustrated horizontal-bore scanner it is also contemplated to have the subject arranged face-up, with the dual breast coil disposed over the exposed breasts of the face-up subject. As another example, in a vertical-bore scanner the subject may be arranged in a standing orientation.

With continuing reference to FIG. 1 and with further reference to FIG. 2, the left-hand portion 22 of the dual breast coil 20 provides at least four left-breast conductors configured to couple with the left breast, and in the illustrated example dual breast coil 20 provides six left-breast conductors 31, 32, 33, 34, 35, 36 configured to couple with the left breast. The left-breast conductors define at least four independent left-breast acquisition channels for acquiring magnetic resonance data from the left breast, and in the illustrated example dual breast coil 20 the six left-breast conductors 31, 32, 33, 34, 35, 36 define six independent left-breast acquisition channels 41, 42, 43, 44, 45, 46 for acquiring magnetic resonance data from the left breast.

The illustrated dual breast coil 20 includes a left superior conductor 31 and a left inferior conductor 32 configured to be positioned superior and inferior, respectively, of the left breast. In the illustrated embodiment, the left superior and left inferior conductors 31, 32 define respective independent left superior and left inferior left-breast acquisition channels 41, 42. In other contemplated embodiments, the left superior and left inferior conductors 31, 32 may be electrically or inductively connected to define a single one of the left-breast acquisition channels.

The illustrated dual breast coil 20 further includes a left anterior conductor 33 and a left posterior conductor 34 configured to be positioned anterior and posterior, respectively, of the left breast. In the illustrated embodiment, the left anterior and left posterior conductors 33, 34 define respective independent left anterior and left posterior left-breast acquisition channels 43, 44. In other contemplated embodiments, the left anterior and left posterior conductors 33, 34 may be electrically or inductively connected to define a single one of the left-breast acquisition channels.

The illustrated dual breast coil 20 further includes a left lateral (side) conductor 35 and a left medial (central) conductor 36 configured to be positioned lateral and medial, respectively, of the left breast. In the illustrated embodiment, the left lateral and left medial conductors 35, 36 define respective independent left lateral and left medial left-breast acquisition channels 45, 46. In other contemplated embodiments, the left lateral and left medial conductors 35, 36 may be electrically or inductively connected to define a single one of the left-breast acquisition channels.

The right-hand portion 24 of the dual breast coil 20 provides at least four right-breast conductors configured to couple with the right breast, and in the illustrated example dual breast coil 20 provides six right-breast conductors 51, 52, 53, 54, 55, 56 configured to couple with the right breast. The right-breast conductors define at least four independent right-breast acquisition channels for acquiring magnetic resonance data from the right breast, and in the illustrated example dual breast coil 20 the six right-breast conductors 51, 52, 53, 54, 55, 56 define six independent right-breast acquisition channels 61, 62, 63, 64, 65, 66 for acquiring magnetic resonance data from the right breast.

The illustrated dual breast coil 20 includes a right superior conductor 51 and a right inferior conductor 52 configured to be positioned superior and inferior, respectively, of the right breast. In the illustrated embodiment, the right superior and right inferior conductors 51, 52 define respective independent right superior and right inferior right-breast acquisition channels 61, 62. In other contemplated embodiments, the right superior and right inferior conductors 51, 52 may be electrically or inductively connected to define a single one of the right-breast acquisition channels.

The illustrated dual breast coil 20 further includes a right anterior conductor 53 and a right posterior conductor 54 configured to be positioned anterior and posterior, respectively, of the right breast. In the illustrated embodiment, the right anterior and right posterior conductors 53, 54 define respective independent right anterior and right posterior right-breast acquisition channels 63, 64. In other contemplated embodiments, the right anterior and right posterior conductors 53, 54 may be electrically or inductively connected to define a single one of the right-breast acquisition channels.

The illustrated dual breast coil 20 further includes a right lateral (side) conductor 55 and a right medial (central) conductor 56 configured to be positioned lateral and medial, respectively, of the right breast. In the illustrated embodiment, the right lateral and right medial conductors 55, 56 define respective independent right lateral and right medial right-breast acquisition channels 65, 66. In other contemplated embodiments, the right lateral and right medial conductors 55, 56 may be electrically or inductively connected to define a single one of the right-breast acquisition channels.

Moreover, in the illustrated dual breast coil 20, the left medial conductor 36 and the right medial conductor 56 are different conductors defining the independent left medial left-breast acquisition channel 46 and the independent right medial right-breast acquisition channel 66, respectively.

This enables closer coupling of the medial conductors 36, 56 with the respective breasts, and also provides separate acquisitions for the left and right breast data.

The dual breast coil 20 further includes other optional features. For example, left and right probe localization grids 70, 72 are optionally included for use in magnetic resonance imaging-based localization of a needle, biopsy probe, or other interventional instrument interacting with a breast. Similarly, left and tight paddles 74, 76 are optionally included to provide breast vibration in the superior-inferior directions to enable magnetic resonance elasticity measurements. The illustrated conductors 31, 32, 33, 34, 35, 36, 51, 52, 53, 54, 55, 56 are diagrammatically indicated in FIG. 2 as single-loop conductors; however, other conductor geometries can be employed, such as multiple-loop conductors, spiral conductors, and so froth. Still further, the specified positioning of the conductors respective to the breast may be inexact—for example, the posterior conductors 34, 54 are optionally arranged offset from the precise posterior position to accommodate the connection of the breast with the torso.

The illustrated dual breast coil 20 has symmetry that promotes comfort of the subject 16 and facilitates manufacturing by enabling certain components of the left-hand and right-hand portions 22, 24 to be optionally interchangeable. If only one breast (e.g., only the left breast, or only the right breast) is to be imaged, then imaging data is acquired from only the corresponding portion 22, 24 of the dual breast coil 20.

With brief reference to FIG. 3, while the illustrated breast coil is a dual breast coil providing independent acquisition channels for the left and right breasts, it is also contemplated to employ a single breast coil. For example, FIG. 3 shows a single breast coil 20' suitable for imaging the left breast. The single breast coil 20' corresponds to the left-hand portion 22 of the dual breast coil 20 without the right-hand portion 24, and includes the six left-breast conductors 31, 32, 33, 34, 35, 36 providing the six independent left-breast acquisition channels 41, 42, 43, 44, 45, 46 for acquiring magnetic resonance data from the left breast.

With returning reference to FIG. 1, a magnetic resonance controller 80 operates the magnetic resonance scanner 10 in accordance with a breast workflow 82 to acquire magnetic resonance data of the left breast via the left-breast acquisition channels 41, 42, 43, 44, 45, 46, or of the right breast via the right-breast acquisition channels 61, 62, 63, 64, 65, 66, or of both the left and right breasts, and the magnetic resonance data is stored in one or both of the memories or memory partitions 26, 28. The collected magnetic resonance data are processed by a magnetic resonance data processor 86 to generate one or more images, one or more spectra, and/or elasticity data that are stored in a processed magnetic resonance data memory 88. A user interface 90 enables a radiologist, medical doctor, or other user to view images, spectra, elasticity data, or so forth. Optionally, the magnetic resonance data processor 86 and/or the user interface 90 provide further post-processing such as classifying lesions as malignant or benign based on the processed spectra and/or elasticity data.

The example breast workflow 82 includes a first sequence 92 producing imaging data for at least two images inherently aligned that the magnetic resonance data processor 86 reconstructs and combines to produce a fused image indicative of tumors, lesions, or other abnormalities of the breast. The data for the at least two images can be collected in an interleaved or sequential manner and under sufficiently similar conditions that voxels of volume images and slices and planes of slice images are all aligned, without shifting or spatially transforming images. For example, the two images that are combined are suitably selected from a group including: (i) a T1 weighted image; (ii) a T2 weighted image; (iii) a diffusion weighted image; and (iv) a contrast dynamic image. As one specific example first sequence 92, the T1 weighted image is omitted and the T2 weighted image, diffusion weighted image, and contrast dynamic image are generated and combined. In another specific example first sequence 92, the T1 weighted image, T2 weighted image, and diffusion weighted image are generated and combined, while omitting the contrast dynamic image. This latter example first sequence 92 advantageously avoids the invasive and time-consuming administration of a contrast agent, and accordingly the acquiring of magnetic resonance data for the generating of the T1 weighted image, the T2 weighted image, and the diffusion weighted image can be performed over an acquisition time spanning less than or about 10 minutes, and typically spanning about 5-6 minutes. In some embodiments, the first sequence 92 acquisition of magnetic resonance data for the at least two images generates images spanning the same volume, so that the combining or fusing of images suitably operates on a voxel-by-voxel basis.

Advantageously, the first sequence 92 image data for each breast are acquired as undersampled magnetic resonance data using the six independent acquisition channels 41, 42, 43, 44, 45, 46, 61, 62, 63, 64, 65, 66, and the image reconstruction performed by the magnetic resonance data processor 86 includes combining the undersampled magnetic resonance data from the at least six independent acquisition channels using SENSE to generate an image. Given the large number of acquisition channels, such acquiring and combining can readily operate with a SENSE factor of at least four.

The fused image produced by the first sequence 92 is used by a radiologist, medical doctor, or other user to locate possible malignant tumors or lesions, or other possible malignant breast abnormalities. If a possible malignant breast abnormality is located using the fused image, then a second sequence 94 is performed to acquire and process magnetic resonance spectroscopy data for a voxel or region of interest corresponding to the detected possible malignancy. Spectral information derived from the magnetic resonance spectroscopy data by the magnetic resonance data processor is used to classify the voxel or region of interest (and hence the corresponding detected possible malignancy) as malignant or benign. Alternatively or additionally, the second sequence 94 includes acquiring and processing magnetic resonance elasticity data (generated using the paddles 74, 76 to produce acoustic waves in the breast containing the voxel or region of interest) for a voxel or region of interest corresponding to the detected possible malignancy. An elasticity characteristic of the voxel or region of interest is derived based on the magnetic resonance elasticity data, and the voxel or region of interest (and hence the corresponding detected possible malignancy) is classified as malignant or benign based on the derived elasticity characteristic.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

The invention claimed is:

1. A breast imaging method comprising:
acquiring magnetic resonance data of one or both breasts of a subject using a dual breast coil coupled with said one or both breasts, the acquiring employing at least four independent channels per breast, the dual breast coil including at least four independent acquisition channels per breast wherein the at least four independent acquisition channels for each breast include acquisition channels defined by (i) at least one conductor positioned anterior of the breast, (ii) at least one conductor positioned posterior of the breast, (iii) at least one conductor positioned above the breast, (iv) at least one conductor positioned below the breast, (v) at least one conductor positioned lateral of the breast, and (vi) at least one conductor positioned medial of the breast, wherein at least one of the four independent acquistion channels is defined by an electrical or inductive coupling between two of the conductors; and
processing the acquired magnetic resonance data to generate elasticity data.

2. The breast imaging method as set forth in claim 1, wherein the acquiring includes (i) acquiring at least some magnetic resonance data as undersampled magnetic resonance data using the at least four independent acquisition channels, and the processing includes (ii) performing image reconstruction including combining the undersampled magnetic resonance data from the at least four independent acquisition channels using SENSE to generate an image.

3. The breast imaging method as set forth in claim 2, wherein the at least four independent acquisition channels for each breast include at least six independent acquisition channels per breast, and the acquiring (i) and combining (ii) operate with a SENSE factor of at least four.

4. The breast imaging method as set forth in claim 1, wherein the processing includes:
generating at least two inherently aligned images including at least two of (i) a T1 weighted image, (ii) a T2 weighted image, (iii) a diffusion weighted image, and (iv) a contrast dynamic image; and
combining the at least two generated images to produce a fused image.

5. The breast imaging method as set forth in claim 4, wherein the generating includes one of:
generating at least the T2 weighted image, the diffusion weighted image, and the contrast dynamic image, and
generating the T1 weighted image, the T2 weighted image, and the diffusion weighted image, but not the contrast dynamic image.

6. The breast imaging method as set forth in claim 4, wherein the acquiring includes:
acquiring magnetic resonance data for the at least two of (i) the T1 weighted image, (ii) the T2 weighted image, (iii) the diffusion weighted image, and (iv) the contrast dynamic image over the same imaged volume, the generating producing images spanning the same volume, the combining operating on a voxel-by-voxel basis.

7. The breast imaging method as set forth in claim 4, wherein the acquiring further includes:
acquiring magnetic resonance elasticity data for a voxel or region of interest located using the fused image.

8. The breast imaging method as set forth in claim 7, wherein the processing further includes:
deriving elasticity information from the magnetic resonance elasticity data; and
classifying the voxel or region of interest as malignant or benign based on the derived elasticity information.

9. A magnetic resonance system comprising:
a magnetic resonance scanner;
at least one breast coil with at least four independent channels per breast operable in conjunction with the magnetic resonance scanner for acquiring magnetic resonance data, wherein the at least one breast coil includes:
at least one anterior conductor positioned anterior of a breast,
at least one posterior conductor positioned posterior of said breast,
at least one superior conductor positioned above said breast,
at least one inferior conductor positioned below said breast,
at least one lateral conductor positioned lateral of said breast, and
at least one medial conductor positioned medial of said breast, wherein at least one of the four independent channels is defined by an electrical or inductive coupling between two of the conductors; and
a processor for processing the acquired magnetic resonance data to generate elasticity data.

10. The magnetic resonance system as set forth in claim 9, wherein the at least one breast coil includes:
at least one left anterior conductor positioned anterior of the left breast;
at least one left posterior conductor positioned posterior of the left breast;
at least one left superior conductor positioned above the left breast;
at least one left inferior conductor positioned below the left breast;
at least one left lateral conductor positioned lateral of the left breast;
at least one left medial conductor positioned medial of the left breast;
at least one right anterior conductor positioned anterior of the right breast;
at least one right posterior conductor positioned posterior of the right breast;
at least one right superior conductor positioned above the right breast;
at least one right inferior conductor positioned below the right breast;
at least one right lateral conductor positioned lateral of the right breast; and
at least one right medial conductor positioned medial of the right breast.

11. The breast imaging method of claim 1, wherein:
the at least one conductor positioned medial of the breast includes a left medial conductor and a right medial conductor which are different conductors; and
the acquiring comprises acquiring magnetic resonance data of both left and right breasts wherein the acquiring of magnetic resonance data of the left breast uses a medial left-breast acquisition channel defined by the left medial conductor and the acquiring of magnetic resonance data of the right breast uses a medial right-breast acquisition channel defined by the right medial conductor and independent of the medial left-breast acquisition channel.

12. The breast imaging method of claim 1, further comprising:
   operating paddles to produce acoustic waves in one or both breasts during the acquiring of magnetic resonance data.

13. The magnetic resonance system of claim 9, wherein the at least one breast coil further comprises:
   paddles arranged to produce breast vibration to enable magnetic resonance elasticity measurements.

14. The magnetic resonance system of claim 9, wherein the at least one breast coil further comprises:
   paddles arranged to produce breast vibration in the superior-inferior direction.

\* \* \* \* \*